United States Patent [19]

Saksena

[11] Patent Number: 5,111,832
[45] Date of Patent: May 12, 1992

[54] PROCESSES FOR THE CONTROL OF TACHYARRHYTHMIAS BY IN VIVO LASER ABLATION OF HUMAN HEART TISSUE

[76] Inventor: Sanjeev Saksena, 33 Fairway Dr., Gree Brook, N.J. 08812

[21] Appl. No.: 636,543

[22] Filed: Dec. 31, 1990

Related U.S. Application Data

[63] Continuation of Ser. No. 559,501, Jul. 24, 1990, abandoned, which is a continuation of Ser. No. 383,225, Jul. 19, 1989, abandoned, which is a continuation of Ser. No. 55,685, May 29, 1987, abandoned.

[51] Int. Cl.$^5$ .............................................. A61B 17/36
[52] U.S. Cl. ........................................ 128/898; 606/2
[58] Field of Search ........................... 606/2, 3, 14, 15; 128/898

[56] References Cited

U.S. PATENT DOCUMENTS

| | | | |
|---|---|---|---|
| 4,266,549 | 5/1981 | Kimura | 606/3 |
| 4,641,912 | 2/1987 | Goldenberg | 128/303.1 K |
| 4,785,815 | 11/1988 | Cohen | 128/303.1 X |

FOREIGN PATENT DOCUMENTS 8502532  6/1985  World Int. Prop. O. .............. 606/3

OTHER PUBLICATIONS

Saksena S, Ciccone J, Chandran P, Pantopoulos D, Lee B, Rothbart ST, "Laser Ablation of Normal and Diseased Human Ventricle", *AM Heart J* 112:52-60 Jul. 1986.

Saksena S, Gadhoke A, "Laser Therapy For Tachyarrhythmias: A New Frontier", *PACE* 9:531-550, Jul.-Aug. 1986.

Ciccone J, Saksena S, Pantopoulos D, "Comparative Efficacy of Continuous and Pulsed Argon Laser Ablation of Human Diseased Ventricle", *PACE* 9:697-704, Sep.-Oct. 1986.

Saksena S, Hussain SM, Gielchinsky I, Gadhoke A, Pantopoulos D, "Intraoperative Mapping-Guided Argon Laser Ablation of Malignant Ventricular Tachycardia", *Am J Cardiol* 59:78-83, 1987.

Saksena S, Gadhoke A, Pantopoulos D, Osypka P, "Radiofrequency Ablation of Arrhythmogenic Diseased Human Ventricle", *Circ* 74-II-461, 1986.

Saksena S, Hussain SM, Gielchinsky I, Gadhoke A, Pantopoulos D, "Successful Mapping—Guided Argon Laser Ablation of Ventricular Tachycardia In Man", *Circ* 74:II-186, 1986.

Saksena S, Hussain SM, Gielchinsky I, Pantopoulos D, Wasty N, Rothbart ST, Alizadeh J, "Intraoperative Mapping—Agon Laser Ablation of Malignant Supraventricular And Ventricular Tachycardia", *J. Am Coll Cardiol* 9:249A, 1987.

Saksena S. Furman R, Gadhoke A, Osypka P, "Feasibility of Radiofrequency Ablation of Supraventricular and Ventricular Tachyarrhythmias", *PACE* 10:414, 1987.

Saksena S, Hussain SM, Gielchinsky I, Gadhoke A, Pantopoulos D, "Laser Ablation of Human Atrium and Accessory Pathways: Experimental Observations and Early Clinical Experience", *PACE* 10:427, 1987.

Saksena S, Rothbart ST, Gadhoke A, Hussain SM, Gielchinsky I, "Anatomic, Hemodynamic and Electrophysiologic Effects of Argon Laser Endocardia Ablation For Refractory Ventricular Tachycardia In Man", *PACE* 10:411, 1987.

*Primary Examiner*—Michael H. Thaler
*Attorney, Agent, or Firm*—Kenyon & Kenyon

[57] ABSTRACT

Tachyarrhythmias are corrected by in vivo ablation of human heart tissue employing laser energy delivered by means of elongated optical fibers in a series of short discrete pulses to sites of tachyarrhythmia foci. The operation may be conducted by a thoracotomy or by means of an optical fiber carried by a catheter passed into the heart via a blood vessel. An argon ion laser is preferred. The processes have been demonstrated successfully in 20 clinical operations pursuant to an experimental protocol.

5 Claims, No Drawings

PROCESSES FOR THE CONTROL OF TACHYARRHYTHMIAS BY IN VIVO LASER ABLATION OF HUMAN HEART TISSUE

This application is a continuation of application Ser. No. 559,501, filed Jul. 24, 1990, now abandoned, which in turn was a continuation of application Ser. No. 383,225, filed Jul. 19, 1989, now abandoned, which in turn was a continuation of parent application Ser. No. 55,685 filed May 29, 1987, now abandoned.

This invention relates to processes for the control of tachyarrhythmias by in vivo ablation of human heart tissue by means of discrete pulses of laser energy. It also relates to surgically incising a heart by such discrete pulses of laser energy. In a broader sense, this invention relates to reducing the risk of what laymen often refer to as heart attacks.

BACKGROUND

By way of background, ventricular fibrillation is one type of tachyarrhythmia. It is an irregular uncoordinated action of the fibers of the heart muscle, which results in a failure of the heart to pump blood. Ventricular tachycardia is another type of tachyarrhythmia and is also an irregularity of the heart muscle, generally characterized by an abnormally fast and altered contraction pattern, which may in some instances itself lead to death in a few minutes. Supraventricular tachycardia occurs in the tissues of the heart above the ventricles, especially in the sinus node, atrium, the atrioventricular (AV) bypass tract, or in the AV node. Such tachycardias, especially ventricular tachycardia, are subject to being accelerated into ventricular fibrillation by a number of known factors and stimuli, and hence their existence poses a latent or overt threat to continued life.

The importance of the foregoing is that ventricular tachycardia may, and ventricular fibrillation does, result in cessation of adequate pump function of the heart and sudden cardiac death. This is the leading cause of death of humans in the United States.

Various therapeutic means for controlling tachyarrhythmias have evolved. These include pharmaceutical compounds and compositions for suppressing tachyarrhythmias, implantable antitachycardia devices, and mechanical surgical procedures for the resection of heart tissue. Cardiac mapping techniques conducted during sinus rhythm and/or during induced tachycardia have made possible the identification of specific zones of heart tissue which are the foci of tachyarrhythmias. Such foci occur in many portions of the heart tissue, varying from person to person, and in normal tissue as well as in diseased tissue. Thus, cardiac mapping is an almost necessary diagnostic technique preceding the use of the inventions described herein but must be performed on each patient on a case-by-case basis.

Although cardiac mapping greatly improved the identification of the location of the foci of tachyarrhythmias, thus improving the success of mechanical resection surgery, most such foci occur where mechanical resection is difficult or impractical to perform. Alternative means for the ablation of tissue containing tachyarrhythmia foci have been attempted, e.g., cryothermia, and electrical energy delivered by means of electrode-bearing catheters. However, the therapeutic efficacy of employing electrical energy for ablation of ventricular tachycardia is still subject to debate among surgeons and physicians.

Thus, an objective of the invention described herein is to furnish a process for ablation of heart tissue which can be visually and electrically guided, and which also may be employed on heart tissue in diverse locations which are not as readily resectable by any other single procedure.

The new process is for the control of tachyarrhythmias in living humans by ablating heart tissue in vivo from at least one site by exposing the heart tissue at the site to a laser beam having sufficient energy and for a sufficient time to create a focal lesion at such site. The site in question is within an area on the inner or outer surface of heart tissue which has been previously located by cardiac mapping as causing an arrhythmia. For example, the site may be on the inside or the outside of a heart's ventricle or atrium, or in the atrioventricular groove. The laser energy is transmitted and precisely directed to the selected site by means of an elongated thin optical fiber, and the laser energy is emitted in a series of short discrete pulses.

The invention also includes the process of employing laser energy transmitted through an elongated optical fiber and delivered in a series of short discrete pulses for making incisions through all or only a portion of heart tissue, in lieu of mechanical surgery employing a scalpel. Thus, in performing a ventriculotomy, the laser energy may be employed to cut through a wall of a heart.

DETAILED DESCRIPTION OF THE INVENTION

Any laser may be employed in practicing the processes, such as gas lasers, including argon ion or carbon dioxide, or the krypton fluoride excimer laser, or a solid laser such as neodymium-doped yttrium-aluminum-garnet. However, currently an argon laser is preferred. It has the advantage that the wave lengths of an argon laser (about 488 and 514 nanometers) is selectively absorbed by the hemoglobin of blood and the myoglobin of the heart muscle. It is hypothesized that it is advantageous to have the wave length of the laser energy selectively absorbed by constituents of the human tissue being treated, and thus the particular type of laser which will optimally serve the intended purpose depends in part upon the nature of such tissue.

The laser energy is transmitted through an elongated fiber, such as glass, quartz or plastic optical fibers, typically 100 to 600 microns in diameter. The diameter selected depends upon the specific purpose, with the larger diameters creating a lesion having a larger diameter. The distal end of the fiber may be plain or polished, or may bear a metal cap having a small-diameter aperture through which the laser beam passes. A plurality of optical fibers of differing diameters and/or design may be employed during any single operation. Typically the elongated optical fiber is disposed within the lumen (i.e., the bore) of a catheter, such as a catheter made of polyethylene terephthalate. In surgical use, the optical fiber is manipulated by a surgeon very much like a hand-held stylus with its distal tip held relatively close to the surface of the tissue to which the laser beam is directed, for example, one or two and up to about 15-20 millimeters from such tissue.

Alternatively, for ablation of tissue on the inside of the heart, a catheter bearing the optical fiber may be inserted into the heart through a blood vessel, usually a vein, and the distal tip of the fiber guided by remote control means to the site to be ablated.

Suitable laser-generating apparatus and optical fibers are already available commercially. However, it is anticipated that refinements in them will be made, and new types of lasers and optical fibers will become available, in the future.

The duration of the pulses and the amount of laser power and energy to be employed depends upon a number of factors, such as the type of laser being employed, the nature of the disease, the location and nature of the heart tissue being treated, whether the tissue is normal or diseased, and the nature of the adjoining tissue structure. With an argon laser, the pulse duration may vary over the range of from about 1/10 to about 5 seconds, the power employed may be in the range of from about 2 to about 50 watts, and the energy delivered per site may be in the range of from about 10 to about 1000 Joules. For example, for superficial vaporization of tissue in the atrium or the area of the AV conduction system, pulse durations in the range of from about 0.3 to about 0.5 seconds, laser power in the range of from about 3 to 5 watts, and energy in the range of from about 10 to about 200 Joules per site, may be employed. However, for incising a ventricle wall or creating focal lesions in ventricular tissue, pulse durations in the range of from about one to about two seconds, power in the range of from about 8 to about 12 watts, and energy in the range of from about 100 to about 1000 Joules per site, are suitable. Approximately similar ranges should be suitable for carbon dioxide or neodymium-doped yttrium-aluminum-garnet lasers. The pulse duration for a krypton fluoride excimer laser should be much shorter, by a factor of 100 or 1000, relative to the pulse duration for an argon laser. Commercially available laser generators often have timer apparatus which permits the setting, and facile changing of the setting, of the duration of the pulse, and of the intervals between the pulses. The intervals between the discrete pulses of laser energy is of lesser importance, and may be in the range of from about 0.01 to about 30 seconds, preferably in the range of from about 0.5 to about 5 seconds.

The laser energy literally vaporizes the heart tissue to which it is directed. The focal lesions which are created by the pulses of laser energy are shallow craters or cylindrical recesses in the tissue of the heart, rather like shallow miniature post holes. The lesions are preferably about two or three millimeters deep. Their diameters are a function partially of the diameter of the laser beam with which they are created, partially of the type of tissue, and partially of whether the tissue is normal or diseased. The desired diameter depends on the location in the heart where the lesions are being created. For instance, smaller lesion diameters are preferred near the AV node, whereas larger diameters are employed in ablating ventricle tissue.

The area of tissue in which focal lesions are to be created varies, depending upon the nature and extent of the tachyarrhythmia which is occurring. It is occasionally rather small, only a few square centimeters, but sometimes the area is much larger, such as 20 square centimeters. It is preferred to create the lesions in some form of a pattern, with the distance between the center lines of the lesions being in the range of from about 2 to about 50 millimeters.

It will be understood by those skilled in heart surgery and the treatment of tachyarrhythmias that the minimum effective, the maximum permissible, and the optimum, of the several process variables referred to herein (e.g., type and power of the laser, energy per site, diameter of the optical fiber, pulse duration, and the desired diameter, depth and spacing of the focal lesions) will vary from human to human, depending upon many factors, including illustratively the nature and severity of the tachyarrhythmia, its location, the nature of the tissue at and adjacent to a site of ablation, and the general physical condition of a specific patient. This lack of uniformity, which is typical in medical science, precludes precise quantitative statements of the ranges of physical parameters which will be uniformly applicable to all humans under all conditions.

The pulsed laser ablation processes described herein have a number of advantages. They are applicable for use on the tissues of any portion of the heart where the source of a tachyarrhythmia may be located, in contrast to other means of ablation of tissue. They appear to be efficacious in all such locations. They produce a virtually bloodless incision, which is of importance in heart surgery. Such processes create a focal lesion, or an incision, in which there is less carbonization of tissue and less coagulation, and in which the distance of tissue damage, measured radially outward by histological studies and by impairment of normal electrical activity of the heart tissue, is less than with a continuous or a sequential continuous laser beam or with electrical ablation processes. There is less risk of inadvertently perforating tissue than when employing a continuous laser system or a laser system requiring greater power. There is also less risk of damage to the distal tip of the optical fiber, which, should it occur decreases the uniformity of the effect on the tissue of the laser beam, and requires more frequent intraoperative changes of the apparatus comprising the optical fiber.

In experimental clinical use, the pulsed argon laser ablation process has been established as efficacious and safe, relative to the past history of new surgical processes generally, and relative to ablation processes employing a continuous laser beam specifically. To date, 20 patients have undergone in vivo pulsed argon laser ablation for the correction of various tachyarrhythmias. These operations were conducted pursuant to an experimental surgical protocol issued by the Food & Drug Administration to the applicant of this patent application. All 20 patients have survived. In 19 of such patients, their various tachyarrhythmias have been corrected and none of the 19 requires postoperative sustaining antiarrhythmic medication. One patient is still on a sustaining regimen of an antiarrhythmic pharmacological agent which is satisfactorily suppressing his arrhythmia. The same agent was unsuccessful in suppressing his arrhythmia prior to the pulsed laser ablation operation.

The apparatus usually employed comprised a 15-watt water-cooled argon ion gas laser manufactured by Laser Ionics, of Orlando, Fla. The laser beam was focused by an optical mirror and prism system into an optical coupler, furnished by Trimedyne Company, of Santa Ana, Calif. A quartz optical fiber was employed, usually having a 300 micron diameter.

The successful in vivo clinical practice of the processes described herein is the culmination of extensive preliminary studies directed to laser energy delivery techniques, the anatomical effects of laser ablation conducted on animal tissue in vitro and later in vivo, and in vitro on resectioned human tissue or on hearts obtained by autopsy, and analyses of the elctrophysiological and hemodynamic effects of laser ablation, concerning which a number of papers have been published. However, such preliminary studies are an essential predicate for a responsible professional to undertake experimental clinical practice in humans of the pulsed laser ablation and incision processes described herein. Surgical science progresses by small incremental steps, but in the pursuit of the goal of the amelioration of the lot of mankind, it is the first successful safe in vivo clinical practice in humans which satisfies that goal.

Having thus described the invention, what is claimed is:

1. A method for the in vivo control of supraventricular tachycardia, ventricular tachycardia or ventricular fibrillation, which method comprises obtaining access to the heart of a living human by open-chest surgery, obtaining access by open heart surgery to an area within said heart, said area comprising diseased heart tissue as being a focus causing supraventricular tachycardia, ventricular tachycardia or ventricular fibrillation, said area having been located by cardiac mapping, said area being in the atrium or in the atrioventricular (A-V) bypass tract of said heart, ablating heart tissue from at least one site within said area by exposing said tissue to a laser beam, said ablating step comprising transmitting a beam of laser energy to said site by means of an elongated, thin optical fiber having a distal end, said beam being visible to the human eye, visually observing said laser beam, manually guiding said distal end of said optical fiber in response to visually observing said laser beam, and manually aiming said distal end to cause said laser beam to impact heart tissue at said site, said beam being emitted in a series of short discrete pulses having sufficient energy and for a sufficient time to create a focal lesion at said site, said ablating creating a focal lesion in which there is less carbonization of tissue, less coagulation, and a lesser radial distance of tissue damage than would occur during an electrical energy ablation process.

2. The process of claim 1 wherein during said ventriculotomy said laser beam is employed to cut through a wall of a heart.

3. The process of claim 1 wherein said laser is an argon ion laser.

4. The process of claim 1 wherein said pulses are in the range of from about 1/10 to about 5 seconds in duration.

5. The process of claim 1 wherein, when creating said focal lesions, said laser discharges are directed to a plurality of specific sites in a pre-determined pattern on one surface of said area.

* * * * *